United States Patent [19]

Smith

[11] Patent Number: 4,813,943
[45] Date of Patent: Mar. 21, 1989

[54] URINARY INCONTINENCE COLLECTOR

[76] Inventor: Samuel C. Smith, 210 Hartman Rd., Newton, Mass. 02159

[21] Appl. No.: 85,805

[22] Filed: Aug. 17, 1987

[51] Int. Cl.$^4$ .............................................. A61F 5/44
[52] U.S. Cl. .................................... 604/329; 604/350; 604/353
[58] Field of Search ................................ 604/349–353, 604/325, 335, 323, 329, 327; 4/144.3; 128/132 R, 138

[56] References Cited

U.S. PATENT DOCUMENTS

| | | | |
|---|---|---|---|
| 2,439,683 | 4/1948 | Broderick | 604/353 |
| 2,573,449 | 10/1951 | Johnson | 604/353 |
| 3,035,579 | 5/1962 | Benovic | 604/353 |
| 3,447,536 | 6/1969 | Snyder | 604/348 |
| 3,626,941 | 12/1971 | Webb | 604/31 |
| 4,085,755 | 4/1978 | Burrage | 604/350 |
| 4,197,849 | 4/1980 | Bostik | 604/352 |
| 4,511,357 | 4/1985 | Steigerwald | 604/335 |
| 4,521,213 | 6/1985 | Steigerwald | 604/335 |
| 4,631,061 | 12/1986 | Martin | 604/329 |

FOREIGN PATENT DOCUMENTS 0000512 of 1879 United Kingdom ................ 604/350

Primary Examiner—John D. Yasko
Assistant Examiner—J. L. Kruter
Attorney, Agent, or Firm—Wolf, Greenfield & Sacks

[57] ABSTRACT

The present application discloses a wearable urinary incontinence collector. It consists of a pair of bags designed and shaped to be worn on the inside thighs of an individual appropriately strapped to the legs. A frontal web covers the groin area and supports the bags in connection with a suitable array of straps. The arrangement is virtually leak-proof and inconspicuous when worn while standing, sitting, or lying.

11 Claims, 2 Drawing Sheets

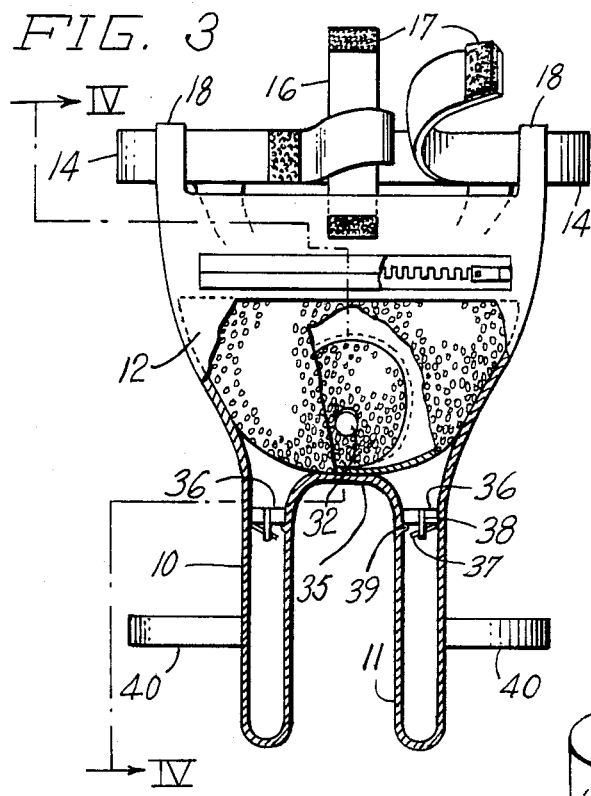
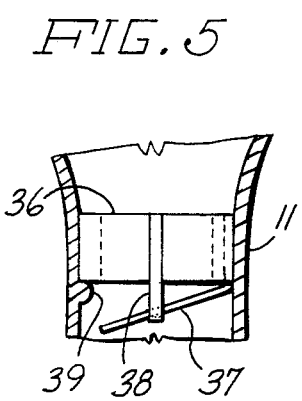
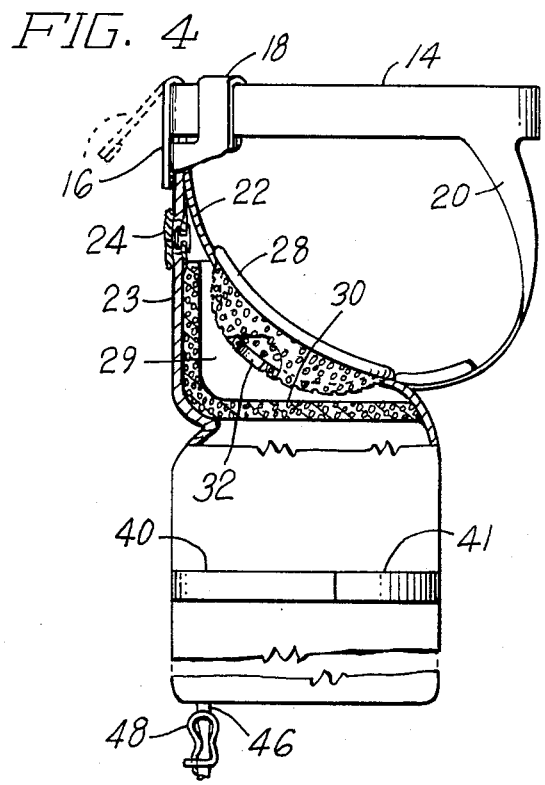
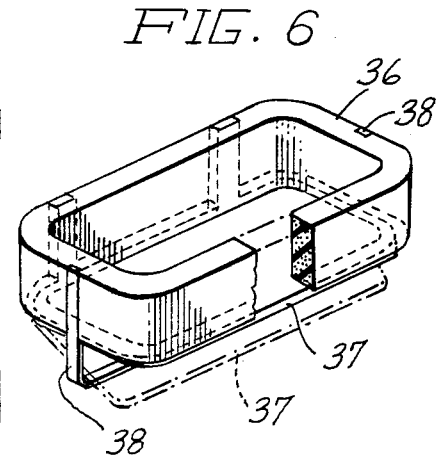

URINARY INCONTINENCE COLLECTOR

SUBJECT MATTER OF INVENTION

The present invention relates to improvements in a urinary incontinence collector for use by those who are incapable of controlling voiding.

BACKGROUND OF INVENTION

The inability to retain urine affects a large number of people of all ages of both sexes. The inability to control one's bladder may create problems for many people under a variety of circumstances. For example, a businessman at a board meeting, travellers, jurors, and many others are placed under very embarrassing conditions if they cannot retain urine even for a short time. There have been a number of efforts to provide suitable devices of this type. However, insofar as I am aware, none suggest the features disclosed and claimed herein. These efforts are exemplified in the following United States patents: U.S. Pat. Nos. D 281,270; D 275,600; D 258,682; D 244,403; D 240,132; D 233,889; D 222,062, O; 4,060,859, X; 4,571,241, X; 4,496,355; 4,304,013; 3,680,543;D 283,922; D 282,489; D 279,605; D 277,410; D 273,709; D 264,133;D 248,168; D 245,543; D 244,403; 3,207,155; 3,636,953; 4,195,630; 4,205,679.

SUMMARY OF INVENTION

Accordingly, it is an object of the present invention to provide an improved urinary incontinence collector that is easy to wear, inconspicuous in appearance and which will function effectively to prevent uncontrolled urinary discharge on one's clothing.

A further object is to provide a collector useful by both male and female that is easily removed, cleaned, and replaced.

A further object is to provide a urinary collector which is particularly suitable for individuals having mild urinary problems as well as those subject to a more serious uncontrolled flow accomplished free of skin wetness and odor.

The assembly consists of a pair of bags, preferably made of thin plastic, joined together below the groin and between the thighs. A front piece of double walled web and a rear v-shaped strap are fastened to a waist band to support the pair of bags. Fastened to the rear wall of the web and partially supported by the rear strap, is a member designed as to accommodate both sexes. This member includes a soft, flexible ring at the periphery of an oval-shaped opening to provide sealing against the urinary orifice. A catch pad of permeable spongy substance is positioned within the double wall which is accessable through a zipper fastener opening. This pad is replaceable and washable as are all other components of the device, except a provided changeable seat pad. A one-way hinged flap in the oval opening serves as a directional valve. In normal position, it stays open; in instances where there is a reverse flow of liquid due to position of wearer, the sensitive valve flap is forced against a spongy seat by the force of the liquid. Any seepage is absorbed by the catch pad. Each bag is provided with a thigh fastening band which is adjustable and stretchable as is the waist band. In essence, a chamber is created such that when worn, the passage of urine is restricted to that chamber (including the related bags) and does not permit the wetness on the exterior or on the wearer.

DESCRIPTION OF DRAWINGS

The foregoing objects and features of the present invention will be better understood from the following detailed description of an illustrative embodiment taken in connection with the accompanying drawings in which:

FIG. 3 is a front partially sectioned view of the urinary incontinence collector illustrating the various components and features of the present invention.

FIG. 4 is a side elevational partial cut-away of the urinary incontinence collector, of FIG. 3 illustrating further assembly features of the invention.

FIG. 5 is a fragmentary sectional side view of the urinary incontinence collector, illustrating the valve features and function, and FIG. 6 is a partial cut-away perspective view of the urinary incontinence collector, illustrating the valve features of the invention.

DETAILED DESCRIPTION OF THE PREFERRED EMBODIMENT

Figure 1:
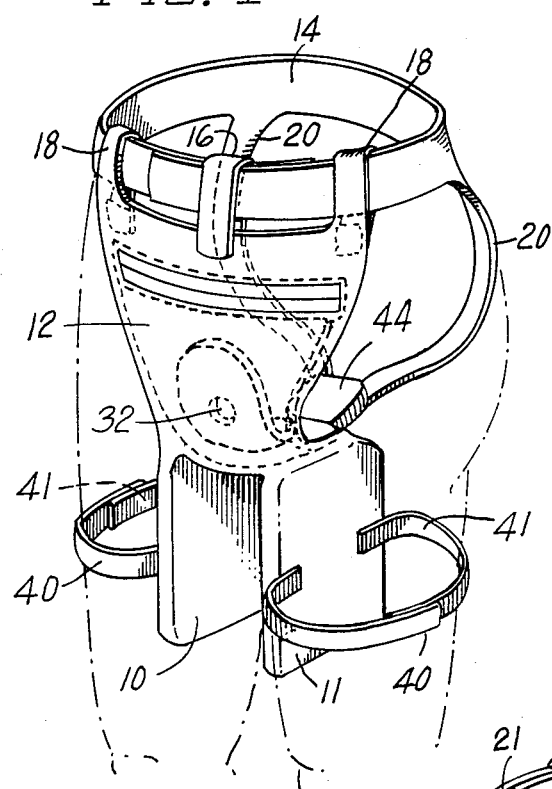
FIG. 1 is a perspective view of a urinary incontinence collector according to the present invention with a torso indicated in dotted outline.
Figure 2:
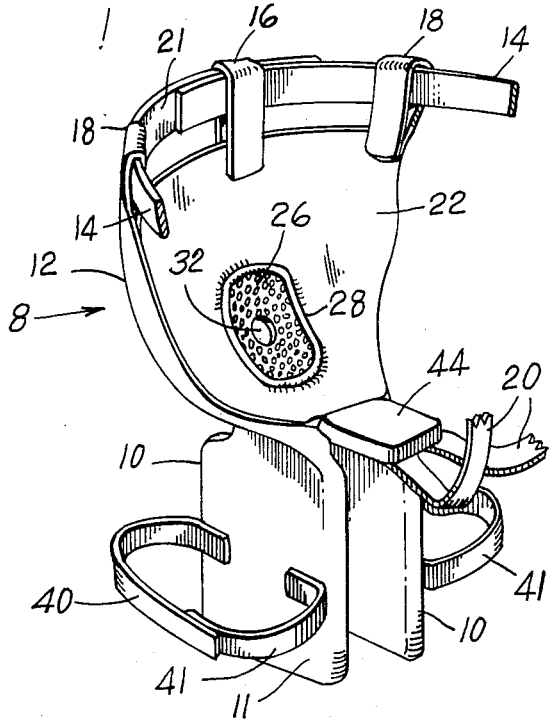
FIG. 2 is a rear fragmentary perspective view of the urinary incontinence collector of FIG. 1, illustrating the various assembly features of the present invention.

The present urinary incontinence collector assembly comprises a pair of bags 10 and 11, the double-walled web 12, waist band 14 secured to the web 12 by loops 16 and 18, and rear support strap 20.

The waist band 14 may be made of suitable fabric and should be adjustable in length. This may be achieved by providing the free ends of the waist band 14 with an appropriate closing mechanism such as the conventionally well known Velcro fastening system 21. The double-walled web 12 consists of a rear wall 22 and a front wall 23. A zipper fastener 24 in the front or forward wall 23 provides a lateral opening for access to the interior of the double-walled 12. The rear wall 22 of the web is formed with an orifice or opening 26 that is bordered by an annular gasket 28 of resilient, cushioning material that is adapted to press firmly against the wearer's groin in an area enclosing the urinary opening. A highly absorbent fibrous pad 30 is positioned between the rear and front walls 22 and 23. This fibrous, absorbent pad faces the opening 26 and provides a fluid absorbent medium. An opening 32 appropriately located within the orifice or opening 26 functions as a penis outlet.

The upper ends of the bags are supported by a web 35 that is secured to the inner surface of front wall 23. Openings are provided to permit the passage of fluid from between the forward and rear walls 22 and 23 into one or both of the bags 10 and 11. Each of the bags 10 and 11 are provided with a valve mechanism best illustrated in FIG. 5. This valve mechanism (as also illustrated in FIG. 6) consists of a rectangular frame 36 to which a flap 37 is hingedly attached and a plastic strap 38 that serves to support and retain the valve flap 37 in the open position shown. The rectangular frame 36 may be either or one homogeneous but resilient material, or semi-rigid with the seating area of the base being resilient.

The sensitiveness of the hinge is attributed to an extremely flexible thin plastic film in the order of 0.003" thick. Said hinge may consist of two (or more) extended strips as shown in FIG. 6 or of a continuous extended strip.

Gravity normally permits a downward movement of the flap 37 in the manner best indicated in FIG. 5. Partial closure, due to position of wearer, has virtually no effect on proper flow operation by virtue of the space above the valve, absorbing characteristic of pad 30 and the sensitivity of the flap hinge. Likewise, a reverse flow will cause the flap 37 to close and any seepage would be absorbed by the pad 30.

The valve member can be bonded in place in a bag. A protrusion 39 facilitates positioning.

The bags 10 and 11 are each provided with straps 40 and 41. These straps are designed to wrap around the wearer's leg at the thigh region to secure the bags 10 and 11, one to each leg. Suitable means such as Velcro fasteners may be provided on the facing surfaces of the straps.

The rear straps 20 may be integrally formed with the belt 14 at their upper end and commonly joined at the lower end to the rear edges of the bags 10 and 11. These straps are adapted to extend over the wearer's buttocks and are designed to secure the double walled web 12 in secure engagement with the groin of the wearer. A pad 44 of absorbent material is provided at the junction of the belts 20.

The various components of this device may be made of suitable non-permeable material except for the absorbent portions. A suitable material is a polyester, but other acceptable plastics may also be used. The fibrous pads 30 and the pad 44 are both removeable, with pad 44 designed for regular replacement. A suitable mechanism may be provided for securing pad 44 to the junction of straps 20. Such a mechanism may comprise a Velcro fastener.

A suitable draining means, as shown in FIG. 4, consists of an elastomer protrusion 46 at a base corner of each bag with an associated quick and easy plastic clamp means 48 permanently attached to the protrusion or protuding tube 46.

While the present invention contemplates in its embodiment the use of Velcro (TM) fasteners, other fasteners may also be used.

The foregoing describes a preferred embodiment of the present invention. However, appropriate variations may be effected within the scope of the present invention. Thus, for example, the present invention embodies converting the device from one that is useful for members of either sex to one that is useful primarily for females simply by the elimination of the penis hole.

Another embodiment is to make available a suitable layer of material to avoid direct contact of wearer's skin to the plastic bag in consideration of those who may be conducive to skin rash or other irritation. Quick and easy attachment with Velcro could be relied on as in other aforestated cases.

I claim:

1. A urinary incontinence collector comprising a pair of fluid impervious bags, a double walled web shaped to enclose the genital of a male or female with one of said webs positioned in facing relation to the pubic area and around the wearer's urinary outlet, fluid absorbent means positioned within the double walled web having a surface with a portion adapted to face directly against the wearer's body and a centrally located opening in said portion through which a penis may be inserted into a chamber formed between the other of said webs and said absorbent means, means providing a passage from within said double walled web to said bags, means for securing said bags, one each to each of the inner thighs of a wearer, means for securing said web against the wearer's groin, valve means between said bag and said web for one-way passage of fluid from said web to said bags further having draining means for each said fluid impervious bags and wherein said double wall web is provided with a reclosable opening in a foward wall for access to said fluid absorbent means.

2. A urinary incontinence collector as set forth in claim 1 having a gasket secured to the rear surface of said web about the periphery of said opening therein.

3. A urinary incontinence collector as set forth in claim 1 wherein said means for securing said web includes a belt adapted to be secured about the waist of the wearer with a plurality of additional straps extending therefrom to the rear portion of said webs and to which loops at the upper section of the front portion of said web are fastened.

4. A urinary incontinence collector as set forth in claim 3 including an absorbent pad at the junction of said straps extending from said belt and the rear portion of said web.

5. A urinary incontinence collector according to claim 1 said means for draining said bags comprises a protruding elastomer tube at or near one lower corner of said bags and incorporating a plastic clamp adapted to securely keep said bags leak-proof.

6. A urinary incontinence collector according to claim 1 wherein said means providing entry to the double-walled space and bags comprises a slide fastener opening.

7. A urinary incontinence collector according to claim 1 wherein each of said bags is provided with a valve means for control of the outward flow of liquid.

8. A urinary incontinence collector according to claim 7 wherein said valve means comprises a rectangular frame to which a flap is hinged on the side proximity to the thigh.

9. A urinary incontinence collector according to claim 8 wherein a strap is provided to secure flap to its opening for restricted travel of said flap as it opens and closes.

10. A urinary incontinence collector according to claim 8 wherein the base of said rectangular frame is resilient for sealing the flap when it is closed against the frame.

11. A urinary incontinence collector according to claim 8 wherein the valve flap is in the order of .003 inch thick.

* * * * *